(12) United States Patent
Ho

(10) Patent No.: US 10,646,400 B2
(45) Date of Patent: May 12, 2020

(54) ELECTROTHERAPY DEVICE CAPABLE OF GRADUALLY INCREASING STIMULATION INTENSITY

(71) Applicant: Hoi Ming Michael Ho, Ontario (CA)

(72) Inventor: Hoi Ming Michael Ho, Ontario (CA)

( * ) Notice: Subject to any disclaimer, the term of this patent is extended or adjusted under 35 U.S.C. 154(b) by 123 days.

(21) Appl. No.: 15/895,004

(22) Filed: Feb. 13, 2018

(65) Prior Publication Data

US 2019/0247273 A1    Aug. 15, 2019

(51) Int. Cl.
*A61N 1/36* (2006.01)
*A61H 39/00* (2006.01)
*G05F 3/16* (2006.01)

(52) U.S. Cl.
CPC ....... *A61H 39/002* (2013.01); *A61N 1/36014* (2013.01); *A61N 1/36021* (2013.01); *A61N 1/36034* (2017.08); *G05F 3/16* (2013.01)

(58) Field of Classification Search
CPC .... A61N 1/08; A61N 1/36014; A61N 1/3603; A61N 1/36125; A61N 1/36139; A61N 1/36142; A61N 1/36146; A61N 1/3615; A61N 1/36153; A61N 1/36157; A61N 1/36189; A61N 1/36192; A61N 1/36196; A61N 1/37; A61N 1/3704
See application file for complete search history.

(56) References Cited

U.S. PATENT DOCUMENTS 4,431,000 A * 2/1984 Butler ................ A61N 1/36014
607/73

* cited by examiner

*Primary Examiner* — Allen Porter
(74) *Attorney, Agent, or Firm* — CIPO IP Group

(57) ABSTRACT

An electrotherapy device capable of gradually increasing the intensity of stimulation is provided with a voltage regulation circuit, which is electrically connected to a DC power supply unit, a control unit, and a pulse output circuit respectively, and can regulate the voltage output to the pulse output circuit according to a control signal received from the control unit, in order for the waveforms of the electrical pulses output from the pulse output circuit to vary in modulated intensity, modulated waveforms, modulated frequencies and modulated rest period durations, and for the output current output from the pulse output circuit to each electrode pad to gradually increase from a low value to a predetermined value. The electrotherapy device can thus stimulate corresponding acupoints on a human body with gradually increasing intensity and thereby simulate the forces and tactile sensations of a typical manual massage on those acupoints by hand.

3 Claims, 14 Drawing Sheets

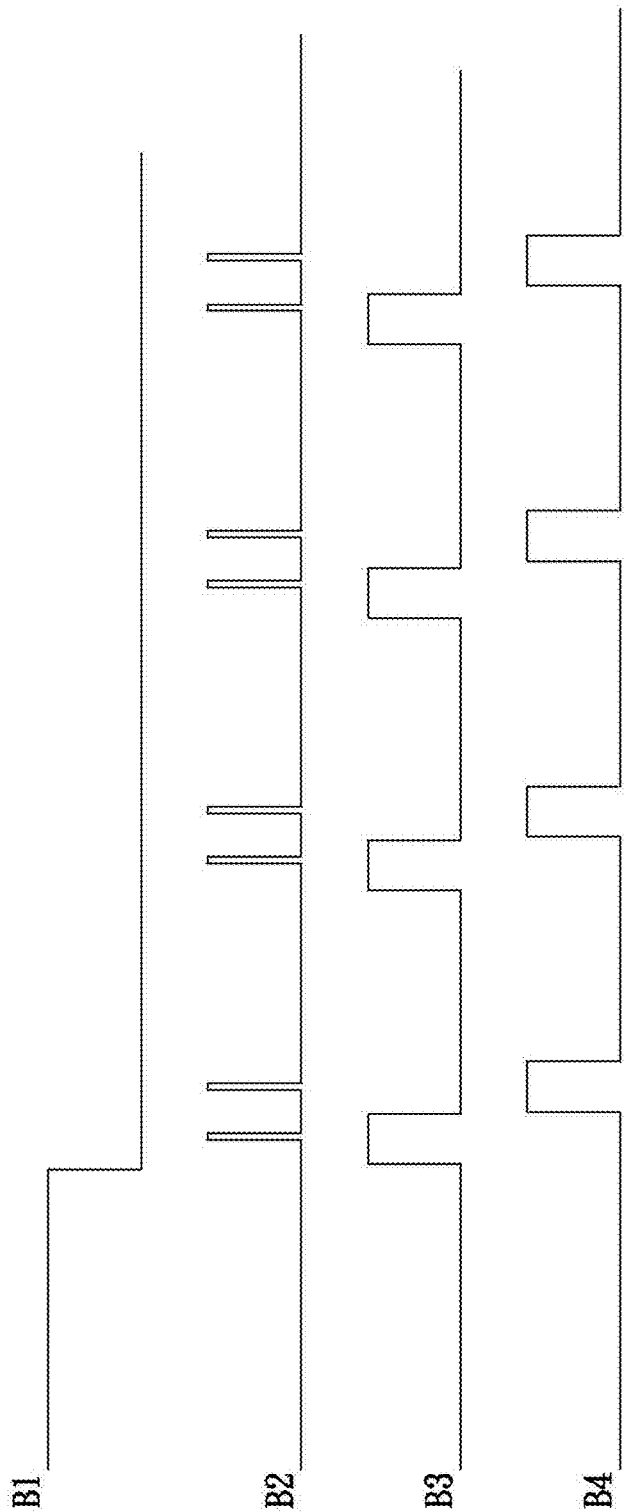

ELECTROTHERAPY DEVICE CAPABLE OF GRADUALLY INCREASING STIMULATION INTENSITY

FIELD OF THE INVENTION

The present invention relates to an electrotherapy device and more particularly to one configured for outputting electrical pulses of various pulse waveforms to achieve a gradual increase in stimulation intensity.

BACKGROUND OF THE INVENTION

Physiotherapy, or physical therapy, plays an important role in both modern and traditional medical science by incorporating such physical factors as light, electricity, water, cold, heat, and force as well as the principle of exercise therapy into the evaluation and treatment of patients. Electrotherapy, in particular, has been an increasingly popular means of treatment due to its efficacy in relieving pain, developing muscle strength, delaying or preventing muscle atrophy, alleviating muscle spasms, and promoting blood circulation in the skin.

Today, electrotherapy can be carried out in many ways including, for example, by low-frequency electrical stimulation (also known as transcutaneous electrical nerve stimulation, or TENS) or medium-frequency interference waves. TENS uses low-frequency waves whose frequency is lower than 1,000 Hz (generally 0~100 Hz). A TENS-based electrotherapy device generates electrical nerve stimulation pulses, which are delivered to and thus stimulate a patient's nerves through electrode pads attached to the patient's skin, with a view to killing pain. Medium-frequency interference waves, on the other hand, are medium-frequency waves whose frequency ranges from 1,000 to 1,000,000 Hz; however, as electric waves generate heat at frequencies higher than 10,000 Hz, medium-frequency waves for clinical use are typically within the frequency range from 1,000 to 10,000 Hz. To apply medium-frequency interference waves, two electrode pads with a frequency difference of 0~100 Hz are generally used (e.g., one at 2,100 Hz and the other at 2,000 Hz). Once the electrode pads are supplied with electricity, medium-frequency waves propagate through the skin and cause electrical interference in tissues deep under the skin, generating low-frequency (0~100 Hz) waves. Thus, by stimulating muscles with an appropriate electric current, effective treatment can be achieved.

Electrotherapy is especially effective in pain relief (e.g., reducing lower-back pain or pain resulting from degenerative arthritis, rheumatoid arthritis, ligament sprain, tendinitis, or the muscle and fascia pain syndrome), and because of that, many patients add electrotherapy to their treatments to reduce medication (e.g., painkillers). Besides, the electrical stimulation of electrotherapy leads to muscle contraction and therefore helps maintain the mobility of muscles and joints. In the light of this, electrode pads have been used to deliver electric waves of the desired waveforms, amplitudes, and frequencies in order to stimulate a patient's to-be-treated body portions, thereby extending the use of electrotherapy to the treatment of soreness and rehabilitation.

Having worked in the technical field of the present invention for years and paid close attention to related technical development, the inventor of the invention found that the existing electrotherapy devices have two typical issues, namely the sensation of painful stimulation causing discomfort and fear to the User, and neural adaptation (i.e. a change (reduction) over time in the responsiveness of the sensory (neurons) system to a constant stimulus) or accommodation by the User's neural motor system, making the electrotherapy stimulation ineffective for pain relief and to facilitate the enhancement of muscle performance as detailed below:

(1) The issue of painful stimulation causing discomfort to the User: As referring to FIG. 1, the conventional electrotherapy devices are generally configured to output electrical nerve stimulation pulses of a predetermined set of waveforms S1~S3, in which each waveform S1~S3 is constructed by a plurality of pulse currents and starts at a constant high level (as in the case of a square wave), meaning a user will suddenly feel relatively strong stimulation, and causing discomfort and painful sensations to the User. This probably explains why some people refuse electrotherapy due to the fear of pain.

(2) The issue of accommodation or neural motor adaptation causing the electrotherapy to be ineffective for pain relief and to facilitate the enhancement of muscle performance: Generally speaking, if the stimulation given to a User during electrotherapy has a constant intensity, waveform, frequency and rest period between each wave, the User's perceived level of intensity of the stimulation and the actual nerve and muscle response to that constant stimulation will reduce with time, even though the intensity of stimulation is actually unchanged. In response to the gradual decline in sensation and neural motor response, the User or the physical therapist performing the electrotherapy would generally increase the intensity or manually change the frequency of the pulse currents applied or manually change the waveform of the pulse currents during the treatment session in order to avoid neural adaptation, but it will be very difficult and inconvenient to the User and the Physical Therapist for performing the additional manual operation of the electrotherapy device in a proper way suitable to the User, if manually changing the intensity, frequency, wave form and rest period duration are not done or not done properly which may lead to an unpleasant and ineffective therapy experience.

The issue to be addressed by the present invention, therefore, is to overcome the aforesaid drawback of the prior art and provide painless and comfortable TENS and EMS stimulations to the User, and to provide preprogrammed modulated TENS and EMS stimulations to the User to avoid neural adaptation for more effective pain relief and enhancement of muscle performance with electrotherapy.

BRIEF SUMMARY OF THE INVENTION

In view of the fact that the existing electrotherapy products are still imperfect in use, not only failing to simulate the sensation and experience of a manual massages, which feature a progressive increase in the force applied, but also having the accommodation or neural motor adaptation issue as a result of their unvarying or constant intensity, wave forms, frequency and rest period duration between each wave, the inventor of the present invention incorporated years of practical experience in research and development into an extensive study with repeated experiments and improvements and finally succeeded in designing an electrotherapy device capable of outputting over 100 variable combination of stimulations with unique sensations, this unique device has the ability of increasing the intensity gradually on it's own and to provide modulating waveforms, modulating frequencies and modulating rest period durations in between each wave of stimulation as disclosed hereinafter in order to provide a painless, comfortable and soothing massage like sensation to the User and to greatly increase the effectiveness of the device to relief pain and to enhance muscle performance by prevent accommodation or neural motor adaptation during the entire treatment period. Furthermore, the User or the Physical Therapist does not need to manually change the intensity, waveform, frequency or the rest period durations during the treatment. The disclosed electrotherapy device is intended to provide better User experience, better pain relief and enhancement of muscle performance than its prior art counterparts.

One objective of the present invention is to provide an electrotherapy device capable of increasing the intensity of stimulation gradually on it's own and to provide modulating waveforms, frequencies and rest time period durations in between each wave of stimulation in order to prevent accommodation and adaptation by the User's neural motor system. The electrotherapy device at least includes a direct-current (DC) power supply unit, a control unit, a pulse output circuit, and at least one pair of electrode pads. The DC power supply unit provides the electric power required for operation of the electrotherapy device. The control unit sends a plurality of control signals to the pulse output circuit so that, once powered by the DC power supply unit, the pulse output circuit generates electrical pulses of predetermined waveforms and send the electrical pulses to each electrode pad. The present invention is characterized in that the electrotherapy device further includes a voltage regulation circuit, which is separately electrically connected to the DC power supply unit, the control unit, and the pulse output circuit. Based on a first control signal received from the control unit, the voltage regulation circuit regulates the voltage it outputs to the pulse output circuit, in order for the pulse waveforms of the electrical pulses output from the pulse output circuit to vary in amplitude, and for the output current of the pulse output circuit to gradually increase from a low value to a predetermined value. Thus, the intensity of stimulation given by each electrode pad to a corresponding acupoint on a User's body will rise progressively, imitating the forces and tactile sensations of a typical manual massage on acupoints by hand.

BRIEF DESCRIPTION OF THE SEVERAL VIEWS OF THE DRAWINGS

The objectives, technical features, and effects of the present invention can be better understood by referring to the following detailed description of an illustrative embodiment in conjunction with the accompanying drawings, in which:

FIG. 10 is a schematic diagram of some other control signals output from the control unit of the electrotherapy device in FIG. 2;

DETAILED DESCRIPTION OF THE INVENTION

Figure 1:
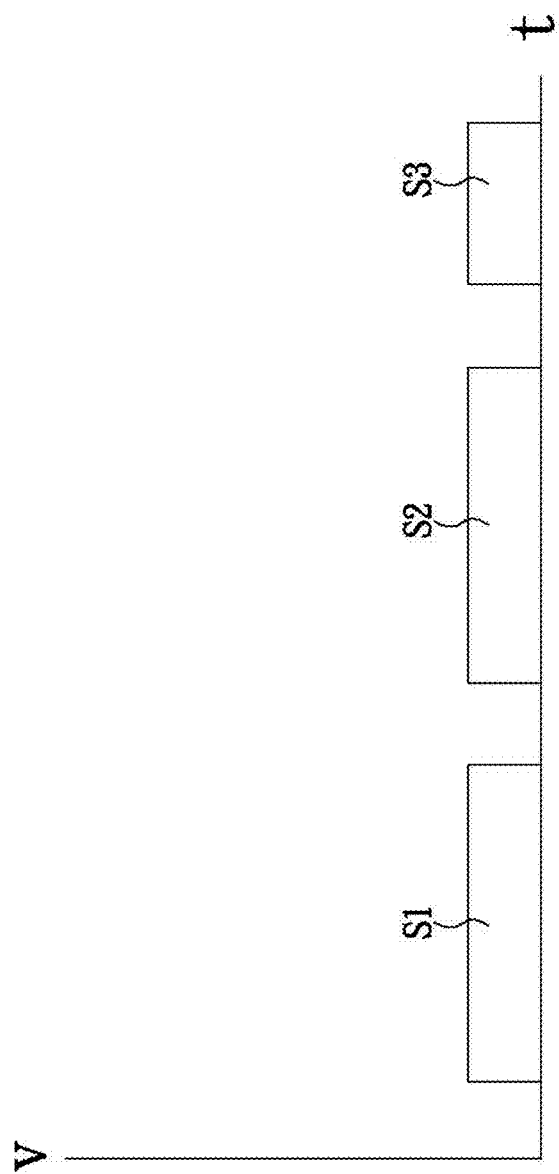
FIG. 1 is a schematic diagram of the waveforms of certain electrical nerve stimulation pulses output from a conventional electrotherapy device.
Figure 2:
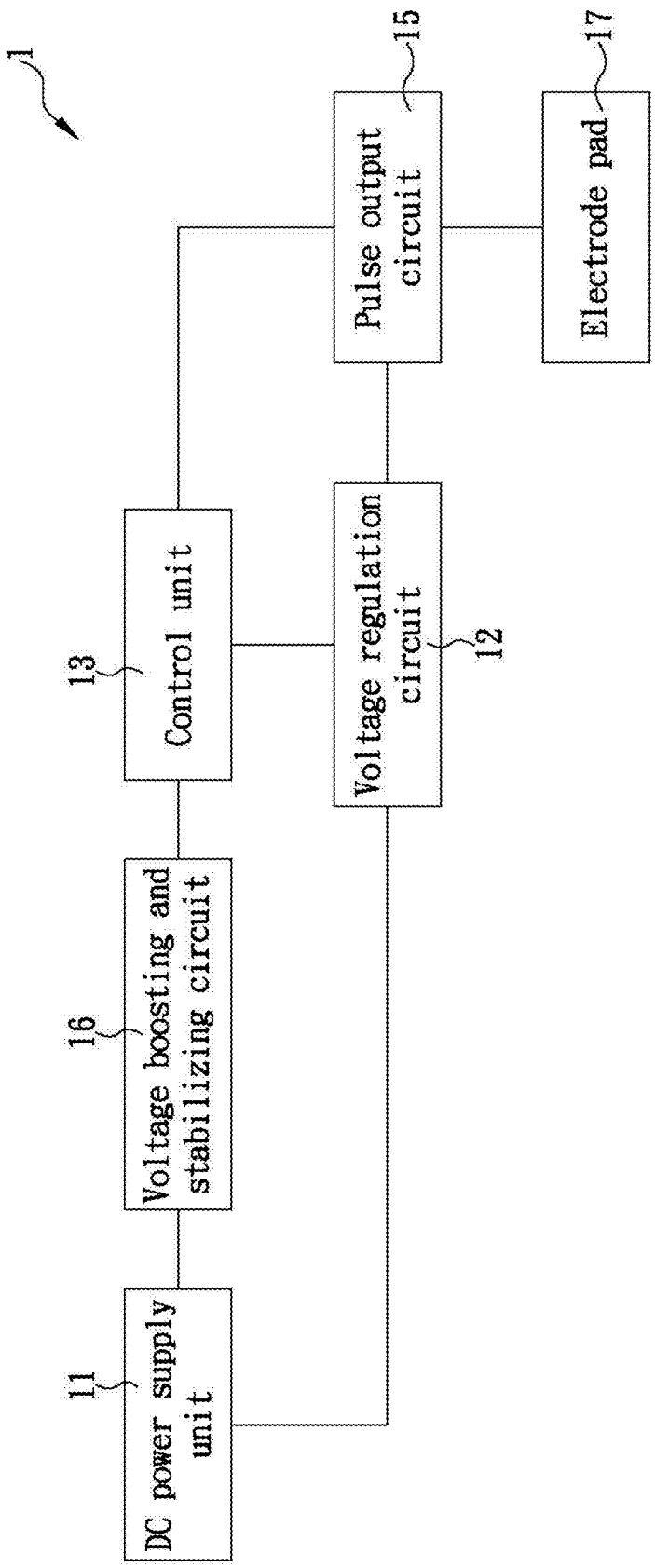
FIG. 2 is a hardware block diagram of the electrotherapy device in an embodiment of the present invention.

According to the applicant's observation, each stroke of an acupoint manual massage generally starts with a gentle force and then gradually increases in force intensity. This gradual increase in force not only reduces the sensation of pain, but also allows the one being massaged to progressively adapt to the forces applied and hence be able to enjoy the comfort of the acupoint manual massage. The applicant incorporated the foregoing features into the present invention, which is an electrotherapy device capable of gradually increasing the intensity of stimulation. Referring to FIG. 2, the electrotherapy device 1 in an embodiment of the present invention at least includes a DC power supply unit 11 (e.g., dry-cell batteries), a control unit 13, a pulse output circuit 15, and at least one electrode pad 17. The DC power supply unit 11 (e.g., batteries) provides the electric power required for operation of the electrotherapy device 1. The control unit 13 is configured to send a plurality of control signals to the pulse output circuit 15 so that, after receiving the electric power supplied by the DC power supply unit 11, the pulse output circuit 15 can generate electrical pulses of predetermined waveforms and send the electrical pulses to each electrode pad 17 in order for each electrode pad 17 to output the electrical pulses and thereby perform the corresponding massaging strokes. Herein, the term "massaging strokes" refers to simulated manual massaging strokes created by varying the interval between each two adjacent electrical pulses, changing the intensity of each electrical pulse, or the like.

It should be pointed out that physical connections between the power supply unit 11, the control unit 13, the pulse output circuit 15, and the at least one electrode pad 17 can be found in the hardware construction of conventional electrotherapy devices, and that the present invention is characterized by the additional technical features described below. With continued reference to FIG. 2, the electrotherapy device 1 in this embodiment further includes a voltage regulation circuit 12. The voltage regulation circuit 12 is separately electrically connected to the DC power supply unit 11, the control unit 13, and the pulse output circuit 15. The control unit 13 is configured to generate a first control signal and send the first control signal to the voltage regulation circuit 12. Based on the first control signal, the voltage regulation circuit 12 regulates the voltage it outputs to the pulse output circuit 15, in order for the pulse waveforms P1 and P2 of the electrical pulses output from the pulse output circuit 15 to vary in amplitude (e.g., each rising gradually from a low level to a predetermined high level, as indicated by the dashed-line circles in FIG. 3), for the output current of the pulse output circuit 15 to gradually increase from a low value to a predetermined value, and consequently for each electrode pad 17 to stimulate a User's body area where the pads are placed (e.g., a corresponding acupoint on the user's body) with gradually increasing intensity, thereby simulating the forces and tactile sensations typical of applying gradual pressure while massaging those acupoints manually by hands.

Figure 4:
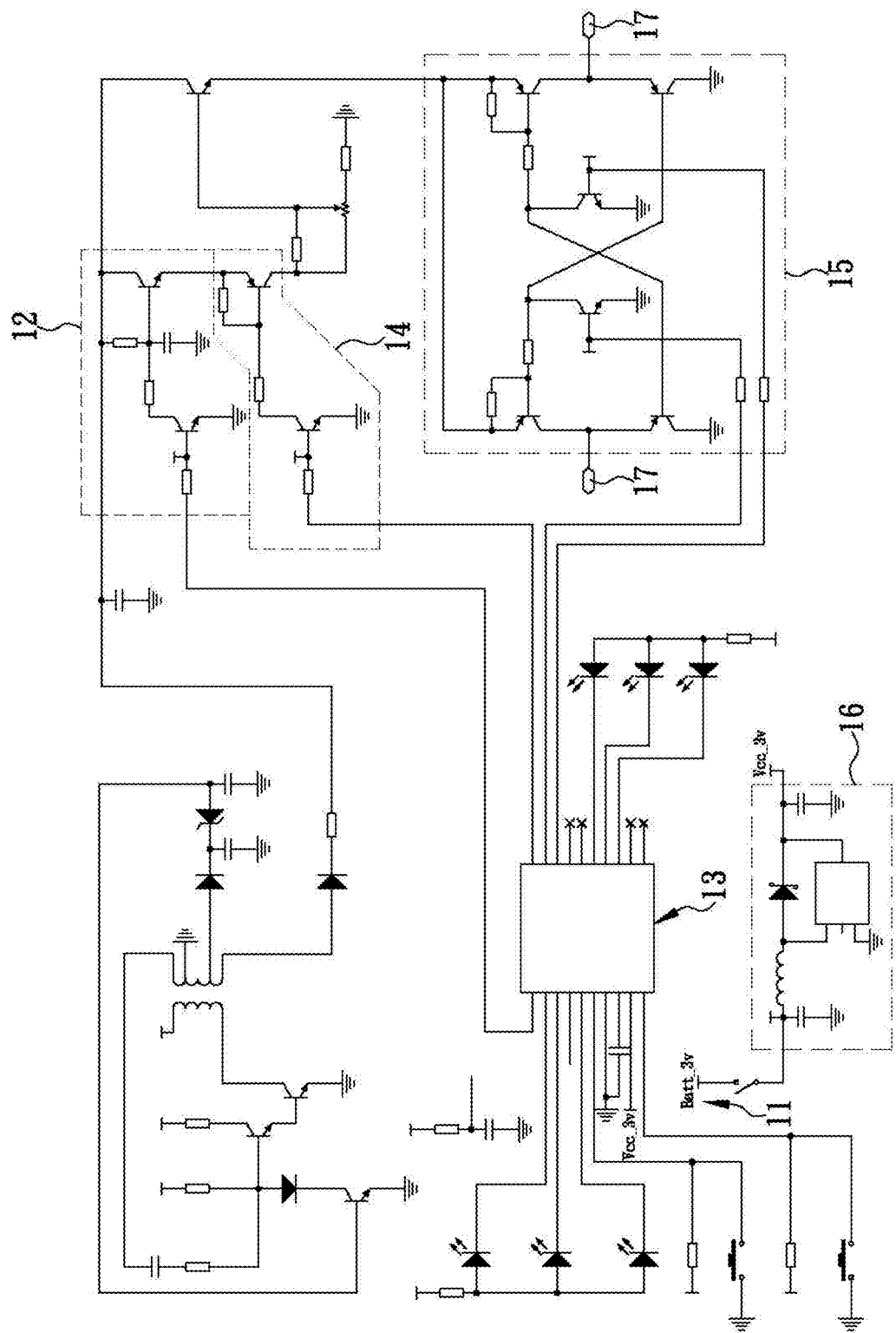
FIG. 4 is a circuit diagram of the electrotherapy device in FIG. 2.
Figure 5:
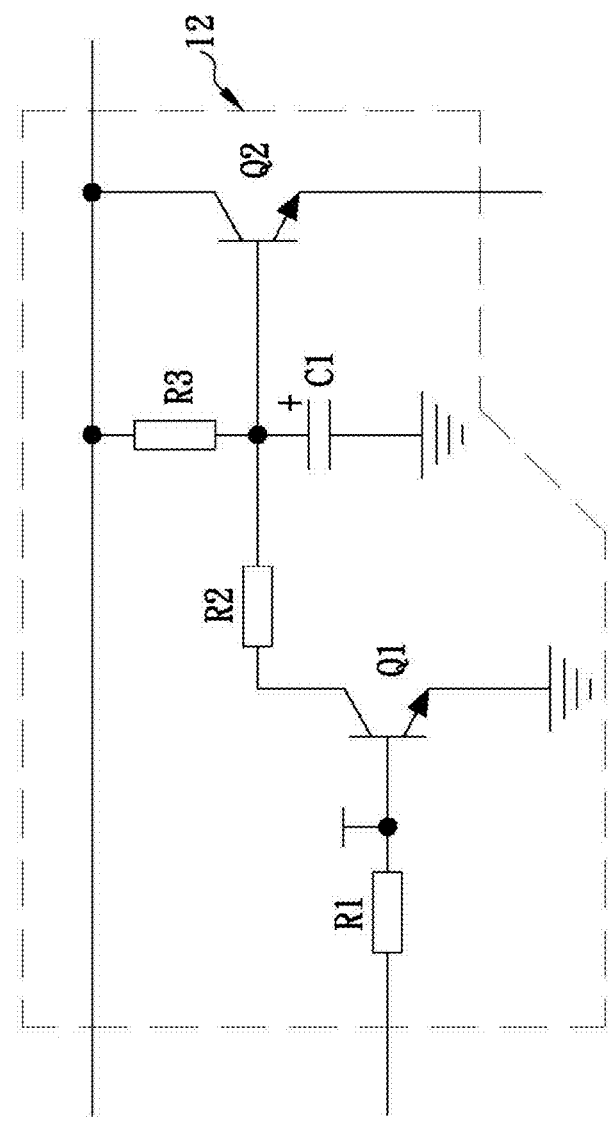
FIG. 5 is a circuit diagram of the voltage regulation circuit of the electrotherapy device in FIG. 2.

To disclose the foregoing technical features in more detail, FIG. 4 shows a circuit diagram of the hardware structure in FIG. 2, and FIG. 5 shows a circuit diagram of the voltage regulation circuit 12. In this embodiment, the voltage regulation circuit 12 includes a first resistor R1, a first transistor Q1, a second transistor Q2, a third resistor R3, and a first capacitor C1. One end of the first resistor R1 is configured to receive the first control signal from the control unit 13. The other end of the first resistor R1 is connected to the base of the first transistor Q1. The emitter of the first transistor Q1 is grounded, and the collector of the first transistor Q1 is connected to one end of a second resistor R2. The other end of the second resistor R2 is connected to the base of the second transistor Q2. The emitter of the second transistor Q2 is connected to the pulse output circuit 15, and the collector of the second transistor Q2 is configured to receive electric power from the DC power supply unit 11. One end of the third resistor R3 is connected to the collector of the second transistor Q2. The other end of the third resistor R3 is connected to the base of the second transistor Q2 and one end of the first capacitor C1. The other end of the first capacitor C1 is grounded.

Figure 3:
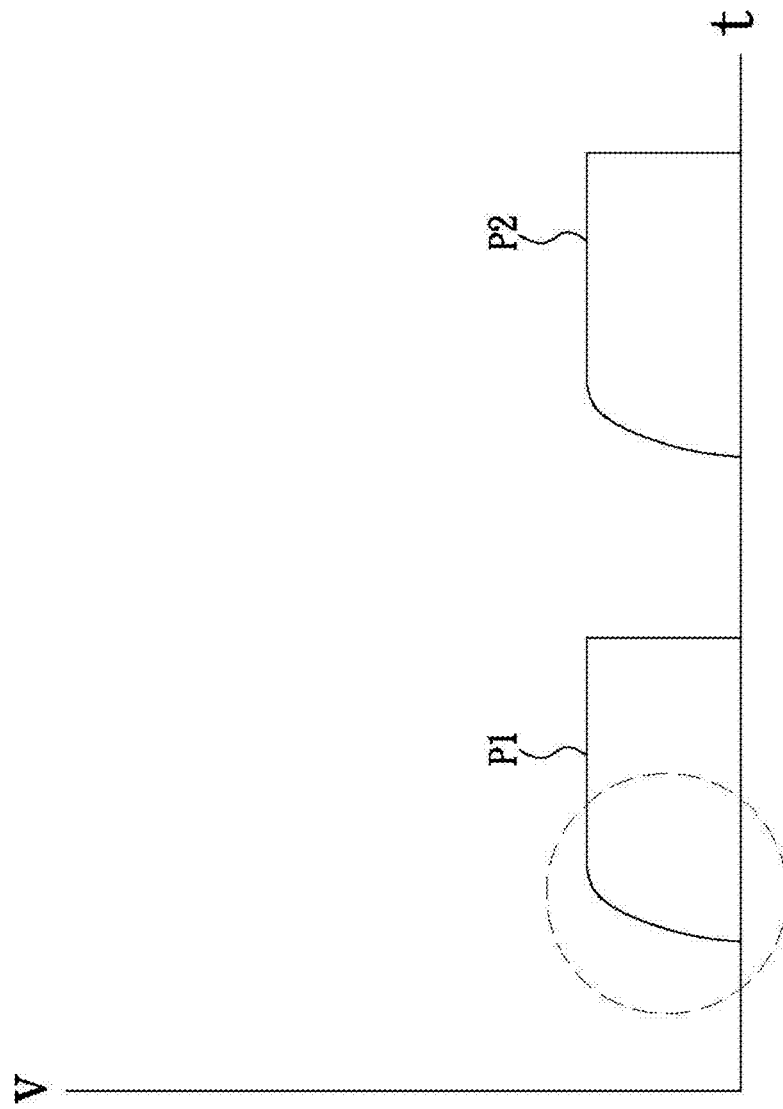
FIG. 3 is a schematic diagram of the waveforms of certain electrical nerve stimulation pulses output from the electrotherapy device in FIG. 2.
Figure 6:
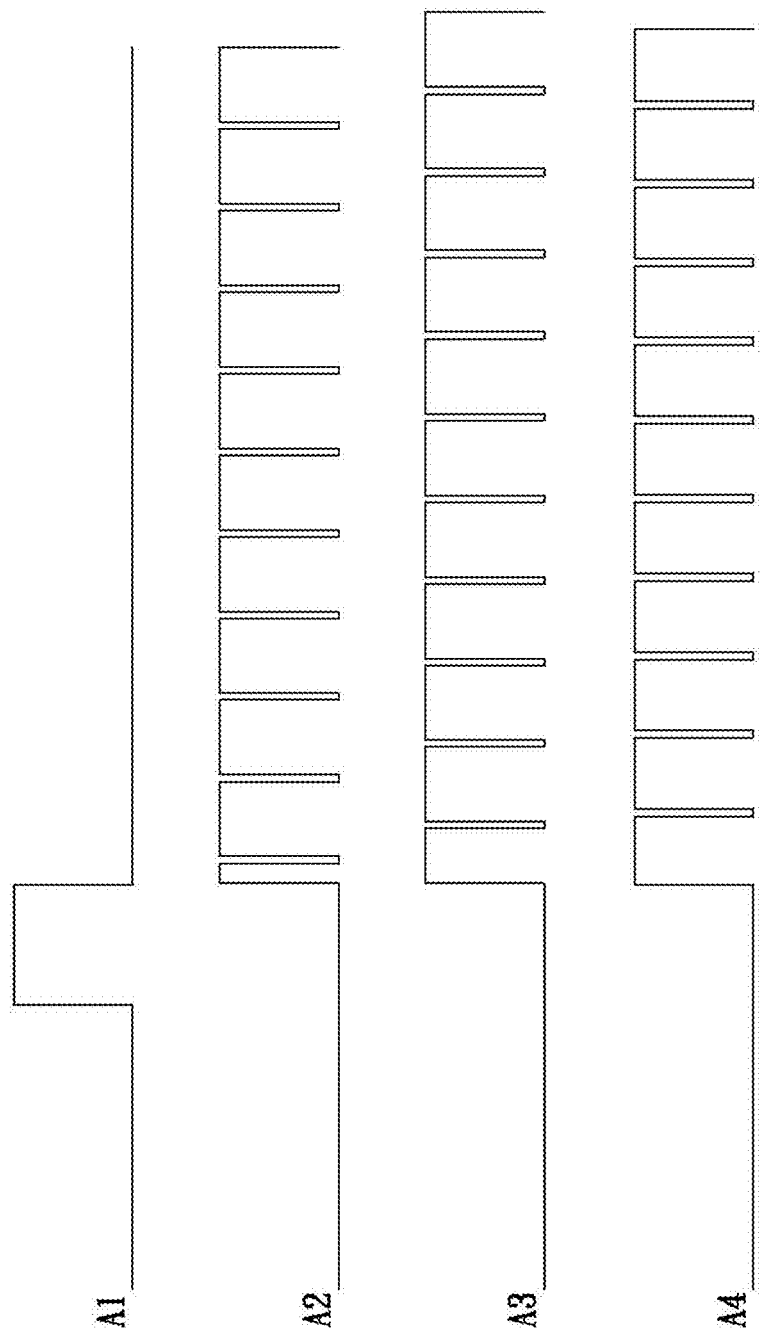
FIG. 6 is a schematic diagram of certain control signals output from the control unit of the electrotherapy device in FIG. 2.

Please refer to FIG. 6 in conjunction with FIG. 4 and FIG. 5. In FIG. 6, which shows control signals output from the control unit 13, the control signal (waveform) A1 is output to the voltage regulation circuit 12, and the control signals (waveforms) A2~A4 are waveforms corresponding to the initial massaging strokes and are output to other circuits (e.g., the pulse output circuit 15). The waveforms corresponding to the initial massaging strokes can combine with one another to generate waveforms corresponding to various final massaging strokes for the user's liking. The working principle of the voltage regulation circuit 12 is stated as follows. Before the first resistor R1 receives the first control signal, the first resistor R1 is in a low-level state, the first transistor Q1 is in a cut-off state, and the first capacitor C1 is in a saturated state. Then (before the waveforms A2~A4 corresponding to the initial massaging strokes are output), a single pulse A1 (i.e., the first control signal) is output to the first resistor R1, bringing the first transistor Q1 into the turned-on state, and the first capacitor C1, in turn, begins discharging. The first capacitor C1 is completely discharged before the pulse comes to an end; as a result, the first resistor R1 returns to the low-level state, and the first capacitor C1 begins to be charged. In the process described above, the second transistor Q2 is turned from the cut-off state to the turned-on state and then from the turned-on state to the amplification state until saturated. The waveforms A2~A4 corresponding to the initial massaging strokes are output when the first capacitor C1 begins to be charged. Thus, a gradual increase of the electric current through the second transistor Q2 causes a change in amplitude of the pulse waveforms output from the pulse output circuit 15 (i.e., the waveforms corresponding to the final massaging strokes), as shown in FIG. 3.

Figure 7A:
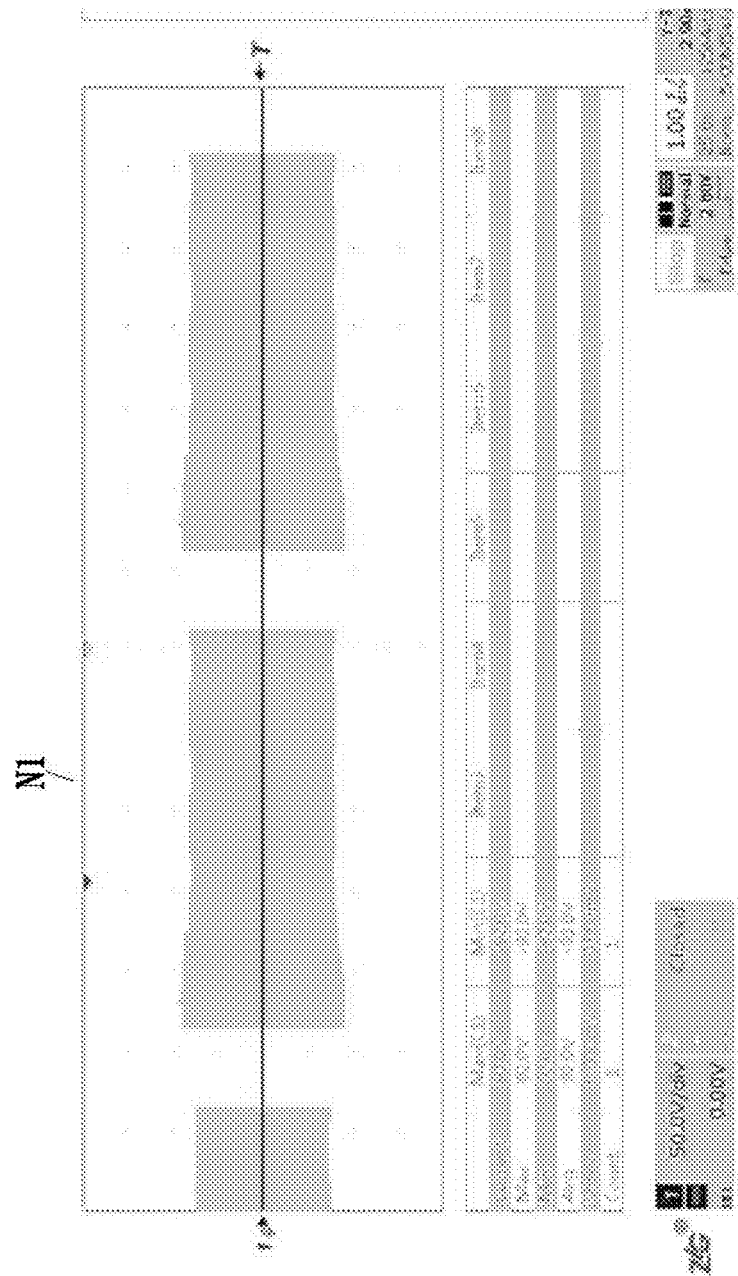
FIG. 7A is an oscillogram showing the pulse waveforms of a conventional electrotherapy product.
Figure 7B:
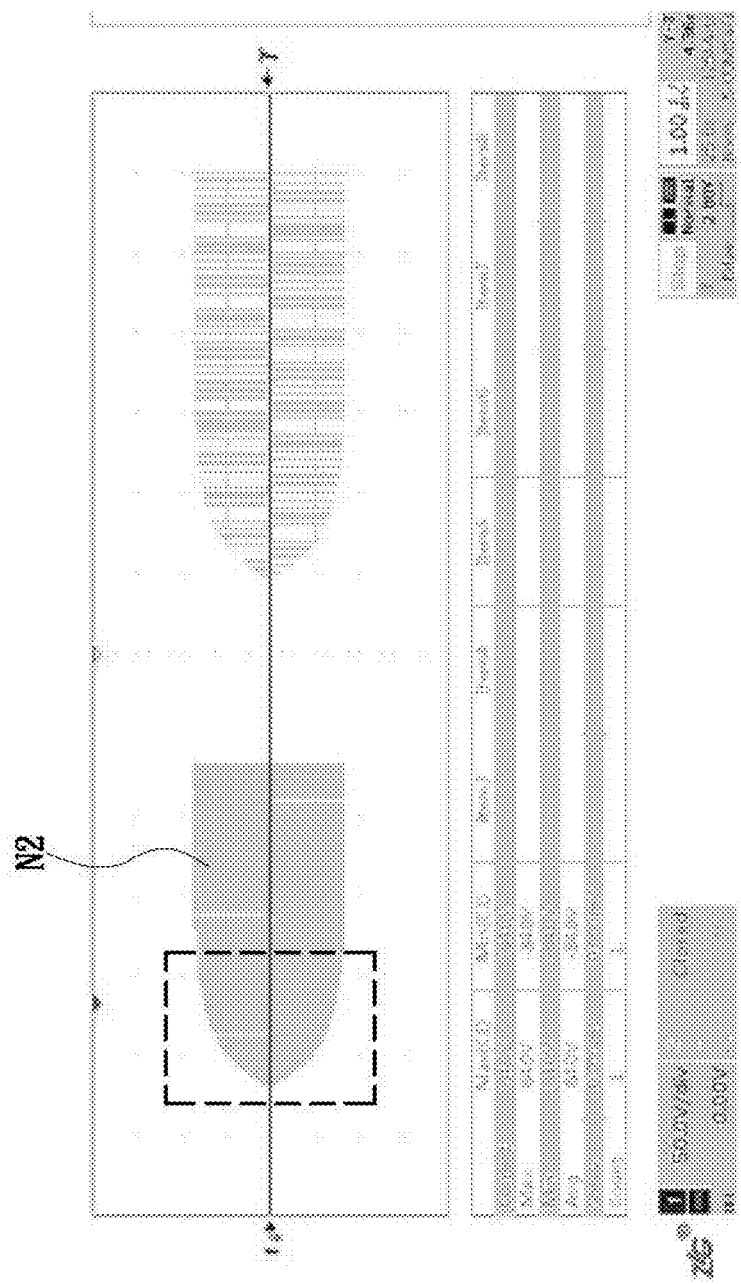
FIG. 7B is an oscillogram showing the pulse waveforms of the electrotherapy device in FIG. 2.

In addition to providing the function described above, the voltage regulation circuit 12 shown in FIG. 4 and FIG. 5 can reduce the disturbance caused by a voltage boosting circuit to the output pulse waveforms, wherein the disturbance occurs at the instant when the electrotherapy device 1 begins to output the pulse waveforms. FIG. 7A and FIG. 7B show the difference between the electrotherapy device 1 of the present invention and a conventional electrotherapy product in this regard. Please note that FIG. 7A and FIG. 7B are screenshots, or more specifically oscillograms, taken directly from the conventional electrotherapy product and the electrotherapy device 1, and that therefore the screenshots include related test data and texts. As FIG. 7A and FIG. 7B are provided mainly for an analysis of the pulse waveforms N1 and N2 shown respectively therein, the test data and texts will not be given further explanation, and nor do they affect the overall technical features of the present invention. Generally speaking, the conventional electrotherapy products are provided with a voltage boosting circuit, and model number HV-F128 of OMRON, whose test result is shown in FIG. 7A and which is referred to hereinafter as the conventional electrotherapy product, is no exception. When the level-up button on the conventional electrotherapy product is pressed to increase the voltage (to 92 V for example), each pulse waveform N1 is disturbed, or more specifically is raised abruptly to a certain level and then becomes stable, as indicated by the dashed-line frame in FIG. 7A. This phenomenon causes an extremely uncomfortable sensation on the User's body where the pads are placed, simply considering the enormous impact made on the body by each pulse waveform N1 output from the conventional electrotherapy product. An elderly User may even be injured by this sudden jolt and corresponding sudden strong muscle contraction as a result. By contrast, referring to FIG. 7B, when the level-up button (not shown) on the electrotherapy device 1 is pressed to increase the voltage (to 84 V for example), the pulse waveforms N2 output from the electrotherapy device 1 rise slowly, as indicated by the dashed-line frame in FIG. 7B. This demonstrates that the voltage regulation circuit 12 is indeed capable of protecting the output pulse waveforms N2 from disturbance from the voltage boosting circuit.

Figure 8:
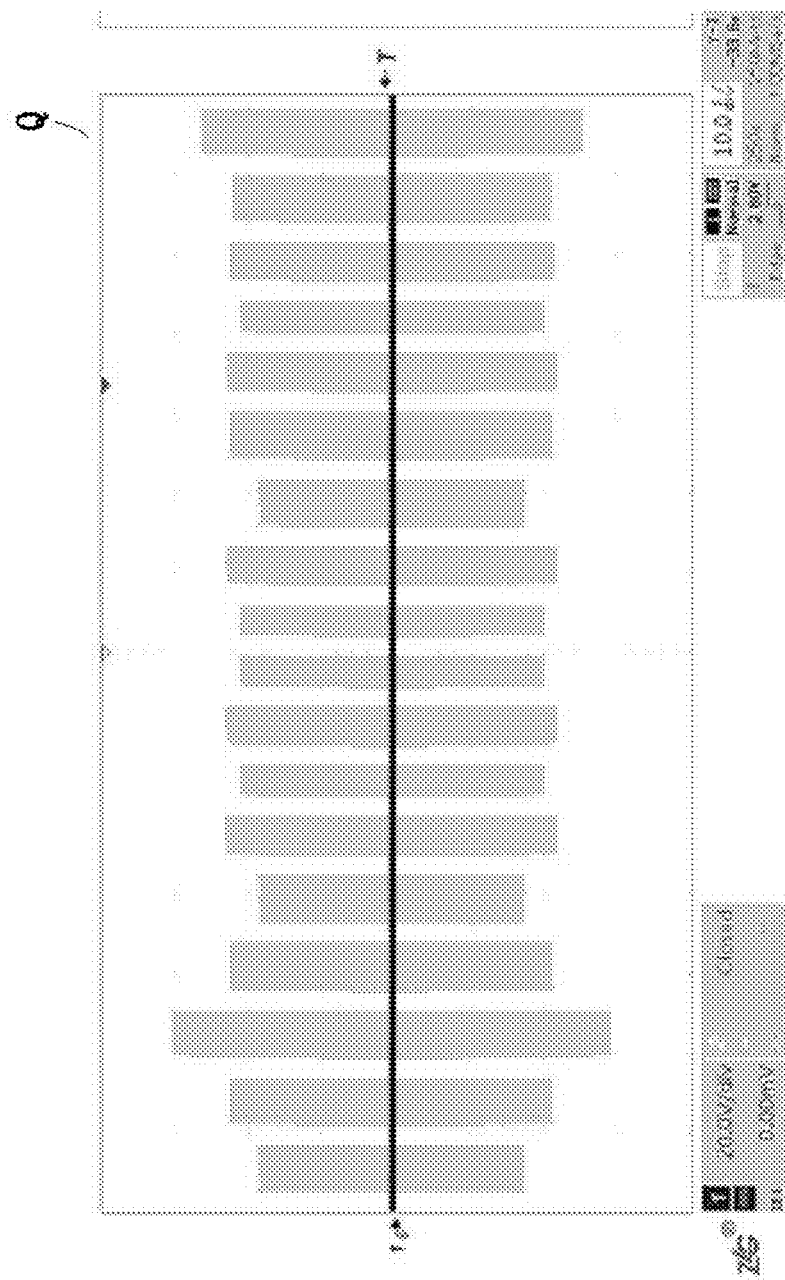
FIG. 8 is another oscillogram showing the pulse waveforms of the electrotherapy device in FIG. 2.
Figure 9:
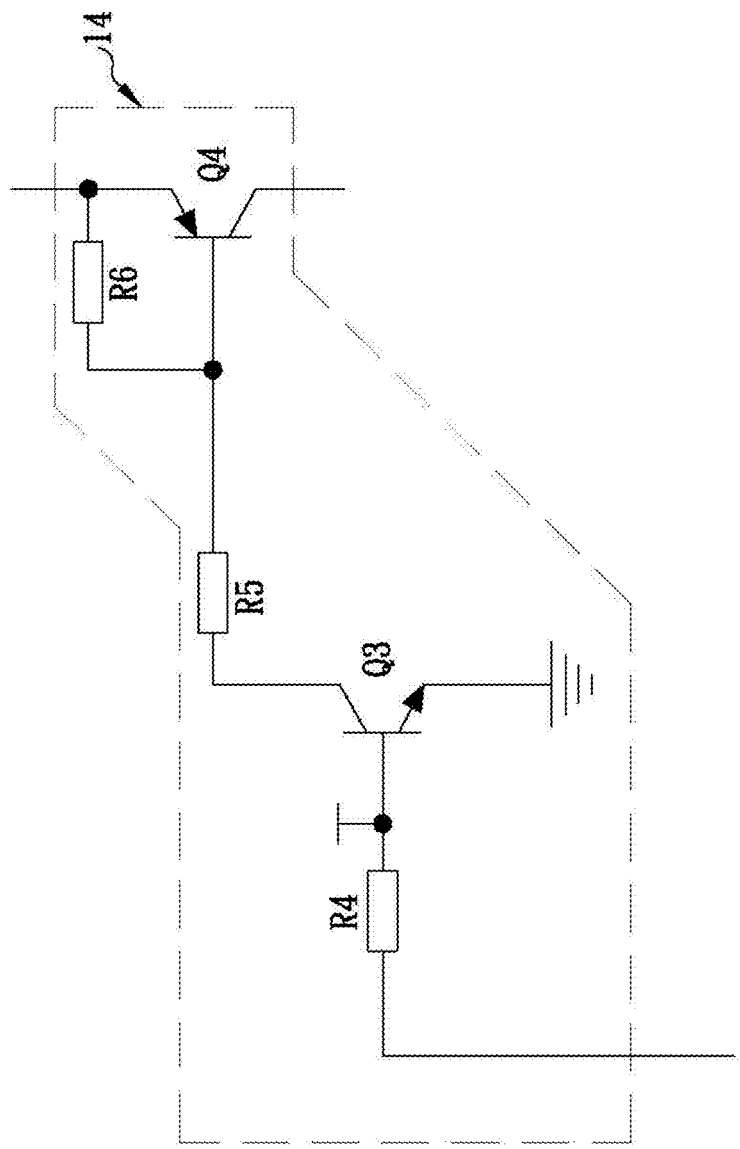
FIG. 9 is a circuit diagram of the output control circuit of the electrotherapy device in FIG. 2.

It should be noted that the conventional electrotherapy products are typically provided only with a circuit structure similar to the pulse output circuit 15. This is largely because the "massaging strokes" of the conventional electrotherapy products are so simple and monotonous that there is no need to output complicated and changing pulse waveforms. The present invention, on the other hand, aims to simulate over 100 variety of "massaging strokes" by outputting a series of complicated and changing pulse waveform Q, frequencies and rest period durations between each wave of stimulation as shown in FIG. 8, and to address the accommodation or neural motor adaptation issue by varying a User's perceived intensity, waveforms, frequencies and rest period durations. To this end, the electrotherapy device 1 is additionally provided with an output control circuit 14, which together with the pulse output circuit 15 at its back end enables the output of complex, changing pulse waveforms Q. In this embodiment, as referring to FIG. 4 and FIG. 9, the output control circuit 14 is separately electrically connected to the voltage regulation circuit 12, the control unit 13, and the pulse output circuit 15 and is configured to receive a second control signal from the control unit 13 and electric power from the voltage regulation circuit 12.

In this embodiment, as again referring to FIG. 4 and FIG. 9, the output control circuit 14 includes a fourth resistor R4, a third transistor Q3, a fourth transistor Q4, and a sixth resistor R6. The fourth resistor R4 has one end configured to receive the second control signal from the control unit and the other end connected to the base of the third transistor Q3.

The third transistor Q3 has its emitter grounded and its collector connected to one end of the fifth resistor R5. The fourth transistor Q4 has its base connected to the other end of the fifth resistor R5, its collector connected to the pulse output circuit 15, and its emitter connected to the emitter of the second transistor Q2. The sixth resistor R6 has one end connected to the base of the fourth transistor Q4 and the other end connected to the emitter of the fourth transistor Q4.

Figure 11A:
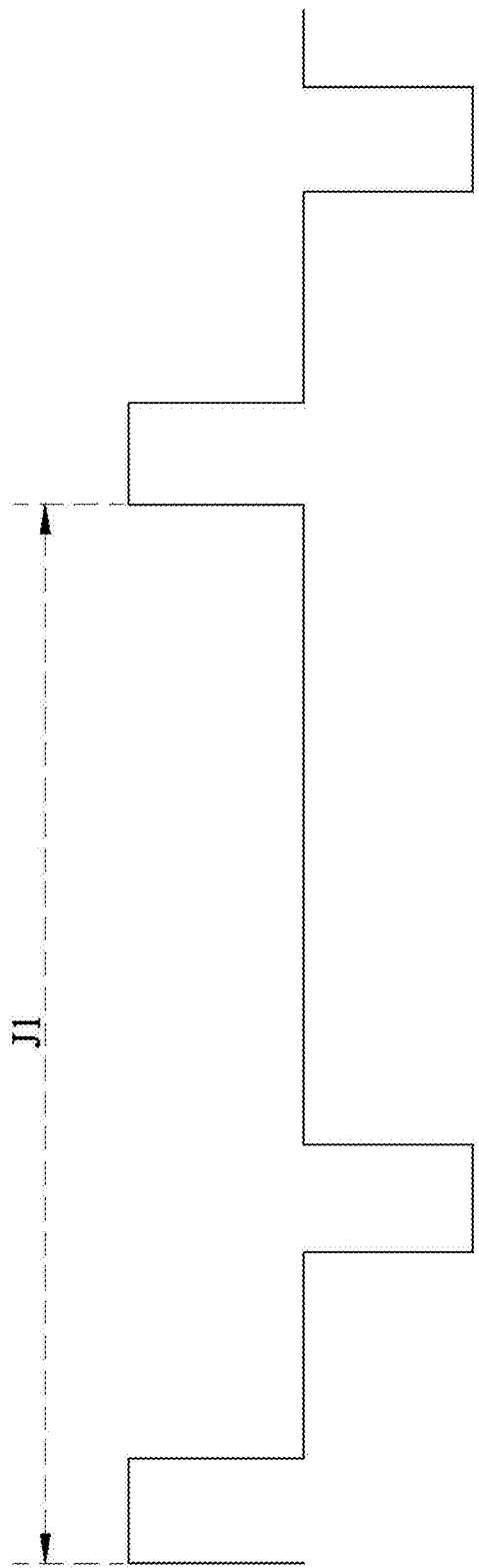
FIG. 11A shows a pulse waveform that can be output from the electrotherapy device in FIG. 2.
Figure 11B:
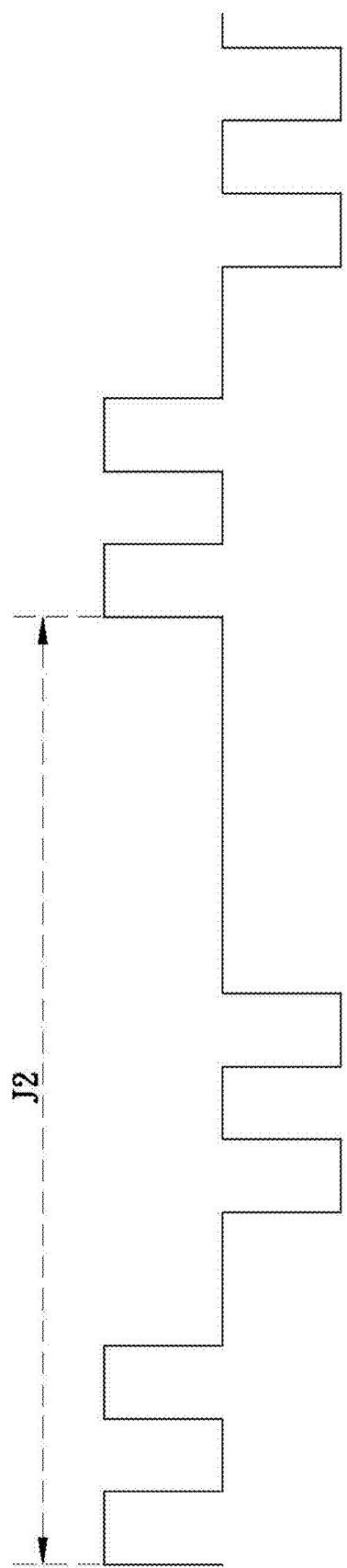
FIG. 11B shows another pulse waveform that can be output from the electrotherapy device in FIG. 2.
Figure 11C:
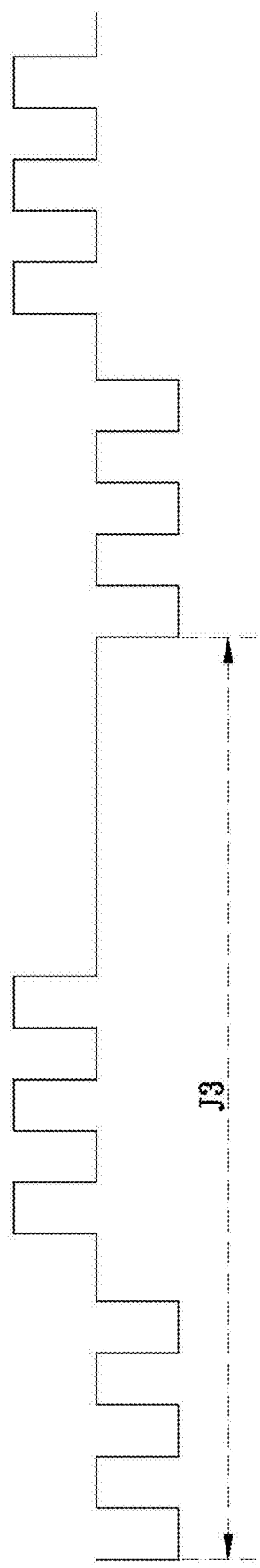
FIG. 11C shows still another pulse waveform that can be output from the electrotherapy device in FIG. 2.

The working principle of the output control circuit 14 is stated as follows. As referring to FIG. 10 in conjunction with FIG. 4 and FIG. 9, the control signal (waveform) B1 is output to the voltage regulation circuit 12, the control signal (waveform) B2 is a waveform corresponding to the initial massaging strokes and is output to the output control circuit 14, and the control signals (waveforms) B3 and B4 are other waveforms corresponding to the initial massaging strokes and are output to outer circuits (e.g., the pulse output circuit 15). The waveforms corresponding to the initial massaging strokes enable the pulse output circuit 15 to output pulse waveforms as shown in FIG. 8 (i.e., the waveforms corresponding to the final massaging strokes). After the fourth resistor R4 receives the second control signal (i.e., the output waveform B2), the second control signal turns on the third transistor Q3 and the fourth transistor Q4 sequentially when at the high level and cuts off the third transistor Q3 and the fourth transistor Q4 when at the low level. Thus, the electric power (i.e., waveform configuration) delivered from the output control circuit 14 to the pulse output circuit 15 is adjusted to vary the pulse waveforms output from the pulse output circuit 15. The combination of the output control circuit 14 and the pulse output circuit 15 makes it possible to effectively imitate not only such massaging strokes as kneading, rubbing, and pounding, but also an increase in force, allowing the Users to feel as if they were given a manual massage on acupoints by hands of a professional masseur. Moreover, in order to simulate various massaging strokes, the electrotherapy device of the present invention must be able to modulate the intensity, frequency, waveform of its pulse currents and output the corresponding pulse waveforms, plus the rest period duration between each wave as shown in FIG. 11A, in which the waveform J1 is repeated at a frequency of 46 Hz and lasts for 5.4 seconds; FIG. 11B, in which the waveform J2 is repeated at a frequency of 30 Hz and lasts for 6.5 seconds; and FIG. 11C, in which the waveform J3 is repeated at a frequency of 15 Hz and lasts for 6.5 seconds. Thus, a User will not feel the same combination of intensity, waveform, frequency, rest period duration of each burst of simulation during the electrotherapy treatment session, and the accommodation or neural motor adaptation issue is solved. With these modulated parameters output with this electrotherapy device, the User or the Physical Therapist performing the electrotherapy will not need to adjust the pulse intensity, waveform, frequency or the rest period duration manually anytime during the entire TENS and EMS treatment in order to get the desired effective pain relief and the enhancement of muscle performance. It should be pointed out, however, that FIG. 11A to FIG. 11C serve only to show different pulse waveforms; the waveforms J1~J3 still feature a gradual increase in output current.

Moreover, to keep the electrotherapy device 1 functional on low battery, the electrotherapy device 1 is further provided with a voltage boosting and stabilizing circuit 16, as shown in FIG. 2 and FIG. 4. The voltage boosting and stabilizing circuit 16 is provided between the DC power supply unit 11 and the control unit 13 and is configured to receive DC power from the DC power supply unit 11 and then output DC power to the control unit 13 at a first voltage (e.g., 3 V). When the voltage of the DC power received from the DC power supply unit 11 is lower than a threshold value, the voltage boosting and stabilizing circuit 16 boosts the received DC power to continue outputting DC power to the control unit 13 at the first voltage. Please note that, in order not to overcomplicate the circuit diagram in FIG. 4, the voltage boosting and stabilizing circuit 16 in FIG. 4 is drawn separately, wherein "Batt_3v" corresponds in position to the DC power supply unit 11 (e.g., batteries) while "Vcc_3v" is connected to the control unit 13.

While the invention herein disclosed has been described by means of specific embodiments, numerous modifications and variations could be made thereto by those skilled in the art without departing from the scope of the invention set forth in the claims.

What is claimed is:
1. An electrotherapy device capable of gradually increasing stimulation intensity, comprising:
   a direct-current (DC) power supply unit configured to provide electric power required for operation of the electrotherapy device;
   a pulse output circuit configured to generate and send electrical pulses of predetermined waveforms after receiving the electric power from the DC power supply unit;
   a control unit configured to generate and output at least one first control signal for a first period of time and at least one second control signal for a second period of time which starts at or later than an end of the first period of time, wherein the first control signal varies pulse waveforms of the electrical pulses in modulated intensity and not in modulated waveforms, modulated frequencies or modulated rest period durations, and the second control signal varies the pulse waveforms of the electrical pulses in modulated waveforms, modulated frequencies and modulated rest period durations, and not in modulated intensity;
   a voltage regulation circuit separately electrically connected to the DC power supply unit, the control unit and the pulse output circuit; configured to:
      receive the first control signal from the control unit;
      regulate a voltage output from the voltage regulation circuit to the pulse output circuit according to the first control signal;
      vary the pulse waveforms of the electrical pulses in modulated intensity based on the voltage regulated according to the first control signal; and
      increase an output current of the pulse output circuit from a low value to a predetermined value gradually based on the voltage regulated according to the first control signal; and comprising:
      a first resistor having a first end configured to receive the first control signal from the control unit, and a second end opposite to the first end, the first resistor being configured to stay in a low-level state before receiving the first control signal;
      a first transistor having a first base connected to the second end of the first resistor, a grounded first emitter, and a first collector, and configured to:
         stay in a cut-off state before receiving the first control signal through the first resistor; and
         enter a turned-on state in response to receiving the first control signal through the first resistor;

a second resistor having a first end connected to the first collector of the first transistor, and a second end opposite to the first end of the second resistor;

a third resistor having a first end connected to the second end of the second resistor, and a second end opposite to the first end of the third resistor;

a first capacitor having a first end connected to the second end of the second resistor and the first end of the third resistor, and a grounded second end opposite to the first end of the first capacitor, and configured to:

stay in a saturated state when the first transistor is in the cut-off state;

begin discharging in response to the first transistor entering the turned-on state;

remain discharging during the first period of time;

become completely discharged and stop discharging before the end of the first period of time;

once become completely discharged, start to be charged by the electric power sent from the DC power supply unit through the third resistor; and continue to be charged during the second period of time;

a second transistor having a second base electrically connected to the second end of the second resistor, the first end of the first capacitor and the first end of the third resistor, a second emitter connected to the pulse output circuit, and a second collector electrically connected to the second end of the third resistor and configured to receive the electric power from the DC power supply unit, and configured to:

during the charging of the first capacitor in the second period of time, undergo state changes including entering a turned-on state from a cut-off state and then exiting from the turned-on state to an amplification state until a saturated state is reached; and raise, via the state changes of the second transistor, an amplitude of the pulse waveforms output from the pulse output circuit gradually from a low level to a predetermined high level as electric current flowing through the second transistor gradually increases;

an output control circuit electrically connected to the control unit and configured to receive the second control signal from the control unit and vary the pulse waveforms of the electrical pulses in modulated waveforms, modulated frequencies and modulated rest period durations based on the second control signal; and at least one electrode pad electrically connected to the pulse output circuit and configured to receive the varied electrical pulses and the gradually increased output current from the pulse output circuit, stimulate at least one corresponding acupoint on a human body with gradually increasing intensity with the varied electrical pulses and the gradually increased output current, and thereby simulate forces and tactile sensations of a typical manual massage on the acupoint by hand.

2. The electrotherapy device of claim 1, the output control circuit being further separately electrically connected to the voltage regulation circuit and the pulse output circuit; further configured to receive electric power from the voltage regulation circuit; and comprising:

a fourth resistor having a first end configured to receive the second control signal from the control unit, and a second end opposite to the first end of the fourth resistor;

a fifth resistor having a first end, and a second end opposite to the first end of the fifth resistor;

a third transistor having a third base connected to the second end of the fourth resistor, a grounded third emitter, and a third collector connected to the first end of the fifth resistor, and configured to:

enter a turned-on state after receiving the second control signal that is at a high level; and enter a cut-off state after receiving the second control signal that is at a low level;

a fourth transistor having a fourth base connected to the second end of the fifth resistor, a fourth collector connected to the pulse output circuit, and a fourth emitter connected to the second emitter of the second transistor, and configured to:

enter a turned-on state after receiving the second control signal at the high level; and enter a cut-off state after receiving the second control signal at the low level; and a sixth resistor having a first end connected to the fourth base of the fourth transistor, and a second end opposite to the first end of the sixth resistor and connected to the fourth emitter of the fourth transistor;

wherein the control unit is further configured to:

sequentially turn on the third transistor and the fourth transistor when the second control signal sent to the output control circuit is at the high level;

bring the third transistor and the fourth transistor into the cut-off states respectively when the second control signal sent to the output control circuit is at the low level; and adjust electric power delivered from the output control circuit to the pulse output circuit and consequently the pulse waveforms output from the pulse output circuit by turning on or bringing into the cut-off states the third transistor and the fourth transistor according to the second control signal.

3. The electrotherapy device of claim 2, further comprising a voltage boosting and stabilizing circuit, wherein the voltage boosting and stabilizing circuit is provided between the DC power supply unit and the control unit and is configured for receiving DC power from the DC power supply unit and outputting DC power to the control unit at a first voltage, and when the DC power received from the DC power supply unit has a voltage lower than a threshold value, the voltage boosting and stabilizing circuit boosts the DC power received in order to keep outputting DC power to the control unit at the first voltage.

* * * * *